United States Patent
Hsiao et al.

(10) Patent No.: US 10,533,962 B2
(45) Date of Patent: Jan. 14, 2020

(54) MINIATURE GAS SENSOR AND METHOD FOR MANUFACTURING THE SAME

(71) Applicant: NATIONAL APPLIED RESEARCH LABORATORIES, Taipei (TW)

(72) Inventors: Yu-Jen Hsiao, Tainan (TW); Ting-Jen Hsueh, Tainan (TW); Yu-Te Lin, Tainan (TW); Yen-Hsi Li, Tainan (TW); Jia-Min Shieh, Hsinchu (TW); Chien-Wei Liu, Douliu (TW); Chi-Wei Chiang, Douliu (TW)

(73) Assignee: National Applied Research Laboratories, Taipei (TW)

( * ) Notice: Subject to any disclaimer, the term of this patent is extended or adjusted under 35 U.S.C. 154(b) by 0 days.

(21) Appl. No.: 15/370,384

(22) Filed: Dec. 6, 2016

(65) Prior Publication Data
US 2018/0038816 A1    Feb. 8, 2018

(30) Foreign Application Priority Data
Aug. 5, 2016   (TW) ............................. 105125077 A (51) Int. Cl.
*G01N 27/12*    (2006.01)
*G01N 33/00*    (2006.01)

(52) U.S. Cl.
CPC ......... *G01N 27/125* (2013.01); *G01N 27/128* (2013.01); *G01N 33/004* (2013.01)

(58) Field of Classification Search
CPC ... G01N 27/125; G01N 33/004; G01N 27/128
USPC .......................................................... 422/90
See application file for complete search history.

(56) References Cited

U.S. PATENT DOCUMENTS

| | | | |
|---|---|---|---|
| 7,495,300 B2 * | 2/2009 | Gardner | G01N 27/128 257/252 |
| 8,293,556 B2 | 10/2012 | Park et al. | |
| 8,361,308 B2 | 1/2013 | Manoukian et al. | |
| 2004/0158410 A1 * | 8/2004 | Ono | G01N 33/004 702/24 |
| 2006/0070890 A1 | 4/2006 | Itoh | |

FOREIGN PATENT DOCUMENTS

| | | | |
|---|---|---|---|
| CN | 101349669 A | | 1/2009 |
| TW | 201115140 | * | 5/2011 |
| TW | 201115140 A | | 5/2011 |

* cited by examiner

*Primary Examiner* — Jill A Warden
(74) *Attorney, Agent, or Firm* — Rosenberg, Klein & Lee (57) ABSTRACT

The present invention provides a gas sensor structure comprising a gas sensing chip. The back of the sensing material is a hollow structure. An insulating layer is below the sensing material. A micro heating is disposed surrounding the sensing material. The sensing material adheres to sensing electrodes. The sensing material is a complex structure including a metal oxide semiconductor and a roughened lanthanum-carbonate gas sensing layer. The thickness of the metal oxide semiconductor is between 0.2 μm and 10 μm; the thickness of the roughened lanthanum-carbonate gas sensing layer is between 0.1 μm and 4 μm; and the size of the back etching holes is smaller than 1*1 mm. By using the gas sensor structure according to the present invention, a suspended gas sensing structure can be fabricated on a silicon substrate and the chip size can be minimized.

20 Claims, 8 Drawing Sheets

S21 — Disposing a metal oxide layer on the heating device

S22 — Coating a lanthanum-containing compound layer on the metal oxide layer to form a sensing layer S24 — Forming a gold-containing metal layer on the lanthanum-containing compound layer, which is on the metal oxide layer, and forming a sensing layer altogether S25 — Annealing the sensing layer, and forming a plurality of nanometer gold dots in the gold-containing metal layer

MINIATURE GAS SENSOR AND METHOD FOR MANUFACTURING THE SAME

FIELD OF THE INVENTION

The present invention relates generally to a gas sensor and the method for manufacturing the same, and particularly to a miniature gas sensor and the method for manufacturing the same.

BACKGROUND OF THE INVENTION

Owing to commercialization and industrialization, more indoor spaces are built and more vehicles are used for satisfying people's needs in leisure, work, and commute. Nonetheless, when people are situated in the confined indoor spaces, pernicious gases will accumulate in the spaces due to air noncirculation, leading to influencing people's living quality in the spaces or, at worst, threatening their lives. In general, when the concentration of indoor carbon dioxide is below 1,000 ppm, it is regarded as normal and the air circulation is good. As the concentration of indoor carbon dioxide is raised to between 1,000 and 2,000 ppm, insufficiency in oxygen, tiresome, and fidgets might occur. When the concentration of indoor carbon dioxide is further increased to between 2,000 and 5,000, adults start to feel uncomfortable, including headaches, somnolence, unconcentration, inattention, increases in heart rate, and slight nausea. When the concentration of indoor carbon dioxide is above 5,000 ppm, exposure to the environment might lead to serious anoxia, which will result in permanent brain damages, coma, or even death. According to the realistic measurement of daily living, the concentration of carbon dioxide can reach around 2,000 to 3,000 ppm once the venting of the indoor air conditioner is insufficient or too many people are in the space. The level of carbon dioxide can start to induce somnolence and cause some minor discomfort. At this time, if the concentration of indoor carbon dioxide is not managed and controlled, it will continue to rise, endangering people in the space.

On the other hand, carbon monoxide is the gas people should pay much attention and control its concentration in their daily lives. Carbon monoxide is a chemical with no color and no smell and produced by incomplete combustion of carbon-containing materials. Accordingly, in our daily lives, incomplete combustion of natural gas or motorcycle exhaust exposes us to carbon monoxide. Due to its higher affinity to hemoglobin than oxygen to hemoglobin by two to three hundred times, as people inhale carbon monoxide, it will compete with the oxygen in human body in combining with hemoglobin and will replace oxygen to combine with hemoglobin. As a result, the oxygen saturation level in the blood will be lowered. Without awareness, people will be losing consciousness and in a coma gradually. Then, their heart and brain will be damaged and, in the end, leading to death. Given the threat on life by carbon monoxide poisoning, early detection of increase in carbon monoxide concentration in confined spaces would be the key point.

Currently, the available commercial gas sensors are mainly infrared gas sensors, which use infrared to provide the energy for stimulating gas and thus changing their temperature, displacement, or frequency. According to the absorption of the infrared by gas and detecting the location of the characteristic absorption peak, the type and concentration of the gas can be judged. Although the accuracy of the measurement results is high, sensing gas by infrared is vulnerable to ambient temperatures. Besides, infrared gas sensors are bulky, costly, and uneasy to be miniaturized, making them difficult in promotion.

In addition, there is another type of gas sensor that detects gases using semiconductors. Metal oxide materials are sintered to form a semiconductor. By maintaining in a high temperature condition using a heater, the metal-oxide semiconductor contacts an inflammable gas. The resistance is expected to be related to the gas concentration. Thereby, carbon monoxide can be detected. Although the required device is simple, this method is prone to the influences of temperature humidity on the circuitry. Besides, the thermoelectric effect of semiconductors will also interfere the accuracy of the detector.

Based on the above description, it is understood that detection of gas concentration is closely related to the safety in indoor spaces. Unfortunately, currently available gas sensors are all limited in applications. Accordingly, how to provide a miniature and accurate gas sensor has become the major technical challenge in the field.

SUMMARY

An objective of the present invention is to provide a miniature gas sensor, which is small in size, sensitive, and applicable to various confined spaces, portable devices, or vehicles with high utility.

Another objective of the present invention is to provide a miniature gas sensor. The sensing material adopted by the gas sensor has high sensitivity, and hence is able to lower the temperature required for the sensing layer during sensing and avoid the bas influence of heat on the sensing process.

In order to achieve the above objectives, the present invention discloses a miniature gas sensor, which comprises a substrate. A dielectric layer is disposed on the substrate and includes a heating device and two electrodes. The sensing layer is disposed on the heating device and connected with the two electrodes. The present invention is characterized in that the sensing layer is formed by a metal oxide layer and a reaction layer, where the reaction layer is disposed on the metal oxide layer.

According to an embodiment of the present invention, the heating device and the two electrodes can be further disposed on the dielectric layer.

According to an embodiment of the present invention, the substrate is a discontinuous structure such that the dielectric layer is built on stilts above the substrate and producing a heat dissipating region not contacting the substrate directly.

According to an embodiment of the present invention, the material of the reaction layer is selected from the group consisting of lanthanum carbonate and nanometer gold.

According to an embodiment of the present invention, the material of the metal oxide layer is selected from the group consisting of tungsten trioxide, zinc oxide, and tin dioxide.

According to an embodiment of the present invention, the material of the heating device is selected from the group consisting of titanium, gold, platinum, silver, and tantalum.

According to an embodiment of the present invention, the material of the dielectric layer is selected from the group consisting of silicon nitride, silicon oxide, and silicon oxynitride.

DETAILED DESCRIPTION

In order to make the structure and characteristics as well as the effectiveness of the present invention to be further understood and recognized, the detailed description of the present invention is provided as follows along with embodiments and accompanying figures.

For solving the problems of current gas sensors, including bulky size, high price, difficulty in miniaturization, and inaccuracy, the present invention provides a novel structure of miniature gas sensor. By using a semiconductor structure as the basis of the miniature gas sensor, the volume of gas sensor can be reduced effectively and hence increasing its applications. In addition, by using lanthanum carbonate or nanometer gold as the sensing material of the semiconductor gas sensor, the sensitivity and the accuracy of the gas sensor can be improved effectively.

Accordingly, the present invention provides a novel structure for miniature gas sensor, which adopts semiconductor as the basis for the gas sensor. The semiconductor structure comprises a heating device. When a sensing material layer is disposed on the heating device, the lanthanum carbonate or nanometer gold contained in the sensing material layer can generate ionized electrons by contacting and reacting with gas. Because the reaction by contacting lanthanum carbonate or nanometer gold with gas is extremely sensitive, the generated voltage change can be measured by the heating and sensing device easily. According to the resistance change, the gas concentration can be deduced, achieving the purpose of high-sensitivity detection.

In the following, the components, the properties, and manufacturing method of the miniature gas sensor according to the present invention will be further described.

Figure 1A:
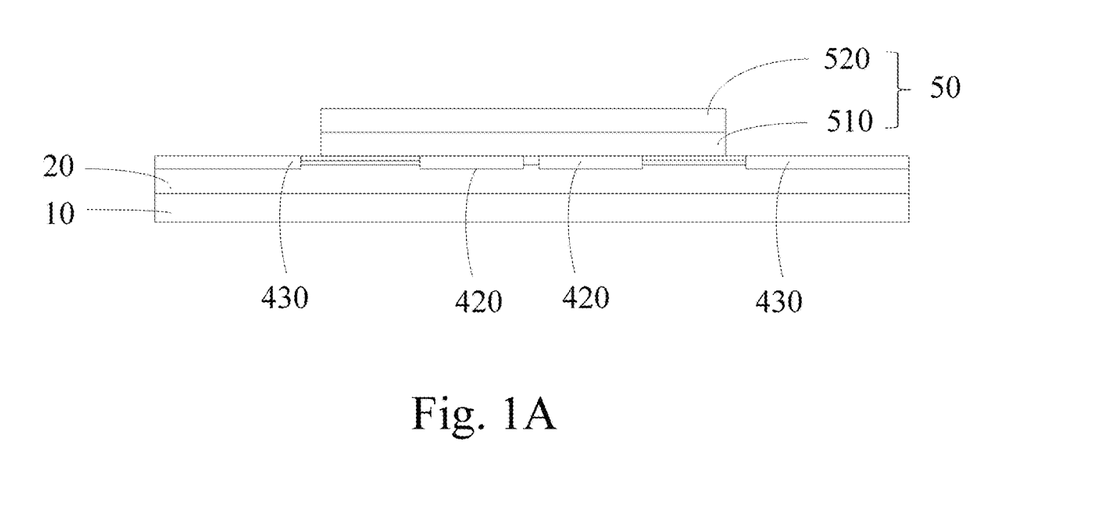
FIG. 1A shows a cross-sectional view according to a first embodiment of the present invention.
Figure 1B:
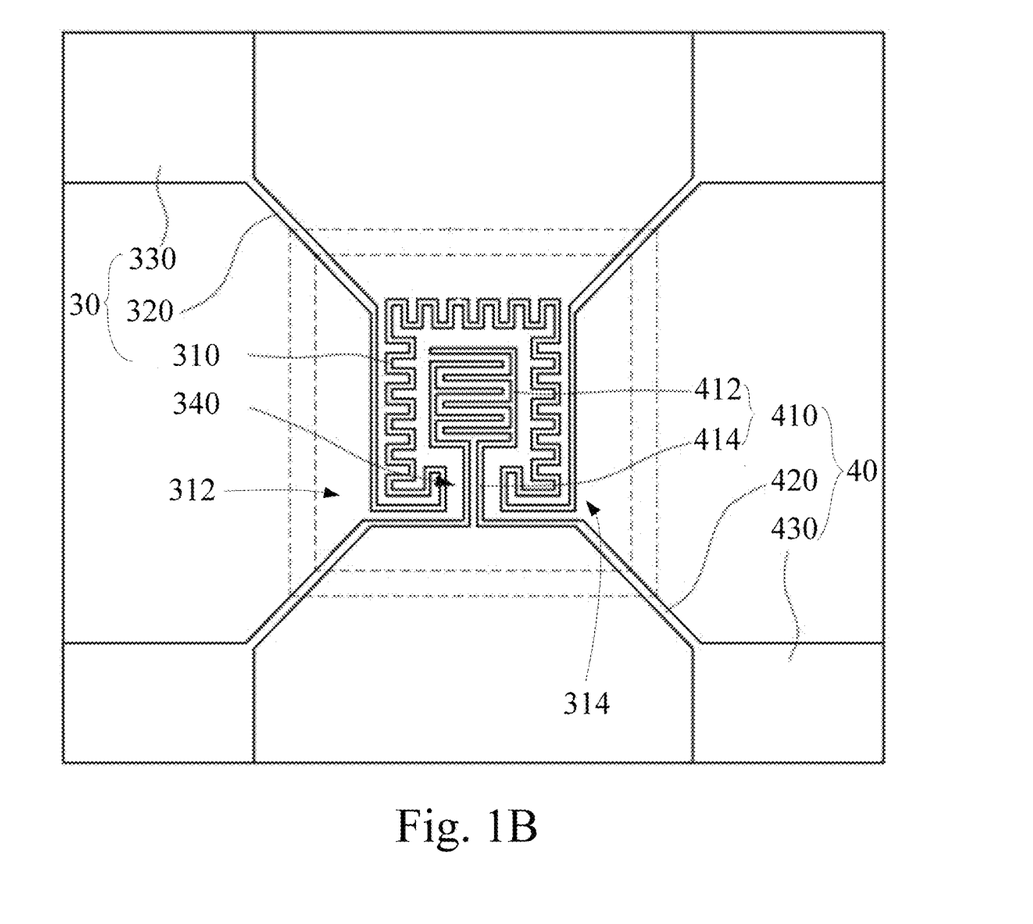
FIG. 1B shows a top view according to a preferred embodiment of the present invention.

Please refer to FIG. 1A and FIG. 1B, which shows a cross-sectional view of the miniature gas sensor according to the first embodiment of the present invention. As shown in the figures, the present invention provides a substrate 10 and a dielectric layer 20. The dielectric layer 20 is disposed on the substrate 10, and includes a heating layer 30 and two sensing electrodes 40. Next, a sensing layer 50 is disposed on the heating layer 30 and connected with the two sensing electrodes 40. The sensing layer 50 is a metal oxide layer 510 and a reaction layer 520. The reaction layer 520 is disposed on the metal oxide layer 510.

Furthermore, the sensing electrodes 40 further including a sensing part 410, two first connecting parts 420 and two electrode pads 430. The sensing part 410 including two interdigitated parts 412 that are staggered and two extension parts 414 parallel disposed on the interdigitated parts 412. The extension parts 414 are connected to the first connecting parts 420 respectively and the first connecting parts 420 are connected to the electrode pads 430 respectively.

Besides, the heating layer 30 further includes a heating part 310, two second connecting parts 320 and two heating pads 330. A plurality of U-shape part arranged in a head-to-tail arrangement to form the heating part 310 and the heating part 310 including a first end 312 and a second end 314. The heating part 310 surrounding the interdigitated parts 412 and forming a notch 340 and the first end 312 and the second end 314 are connected to the second connecting part 320 respectively. The second connecting parts 320 are connected to the heating pads 330 respectively.

Based on the above sensor structure, the gas sensor provided by the present invention can adopt different materials for the reaction layer 520 to sense different gases. The details will be described as follows.

According to the miniature gas sensor provided by the present invention, when the material of the reaction layer 520 is lanthanum carbonate, detection of carbon dioxide can be performed. This is because as oxygen ions (O2-) react with high-concentration carbon dioxide, carbonate ions (CO32-) will be formed, as shown in Equation 1. Then, the carbonate ions will contact and react with the lanthanum carbonate in the reaction layer, producing lanthanum carbonate, oxygen, carbon dioxide, and free electrons, as shown in Equation 2. At this moment, the free electrons will increase the surface conductivity of the sensing layer 50 and lower the resistivity. In addition, the resistance will decrease as the concentration of carbon dioxide in the ambient increases. According to the variations, the concentration of carbon dioxide in the environment can be deduced and thus achieving the purpose of the gas sensor according to the present invention. Besides, as the concentration of carbon dioxide in the air decreases, the ionized carbonate ions in the environment will not be sufficient to react with the lanthanum carbonate in the reaction layer to produce electrons. Then the free electrons in the sensing layer 50 produced during the sensing process will return to the reaction layer and the resistance of the sensor will recover to the initial condition for the next sensing for gas concentration.

$$CO_2 + O^{2-} \rightarrow CO_3^{2-} \quad \text{(Equation 1)}$$

$$La_2O_2CO_3 + CO_3^{2-} \rightarrow La_2O_2CO_3 + \tfrac{1}{2}O_2 + CO_2 + 2\ e^- \quad \text{(Equation 2)}$$

In addition, according to the miniature gas sensor provided by the present invention, as the material of the reaction layer 520 is nanometer gold, carbon monoxide detection can be performed. When the carbon monoxide increases and the temperature is increased accordingly, carbon monoxide will decompose into carbon dioxide and free electrons, as shown in Equation 3. The decomposed free electrons will also increase the surface conductivity of the sensing layer 50 and reduce the resistivity. Similarly, the resistance will decrease as the concentration increases. Thereby, the concentration of carbon monoxide in the environment can be detected.

$$CO + O^{2-} \rightarrow CO_2 + 2\ e^- \quad \text{(Equation 3)}$$

According to the miniature gas sensor as described above, the substrate 10 provided by the present invention is used for carrying the semiconductor miniature gas. In order to maintain the fundamental physical properties of the substrate material during the manufacturing process and not to change due to high temperatures, the substrate material with sufficient stability in high-temperature operating environments is adopted. In addition, to avoid the substrate material from influencing the conductivity of the overall chip structure and further misleading gas sensing, the substrate material should not be conductive. Based on the above properties, the substrate 10 provided by the present invention can be further selected from the group consisting of glass, silicon, and quartz.

According to the miniature gas sensor as described above, the dielectric layer 20 disclosed in the present invention is used for electrically insulating the multi-layer structure of semiconductor and enhancing the sensing efficiency of the miniature gas sensor. The material of the dielectric layer 20 is an insulator in most cases. When an external electric field is applied, the electrons, ions, or molecules will be polarized, and thus increasing the capacitance of the miniature gas sensor. Based on the above property, the dielectric layer 20 provided by the present invention can be further selected form the group consisting of silicon nitride, silicon oxide, or silicon oxynitride. Preferably, silicon nitride and silicon oxide are adopted. Besides, the silicon nitride material is coated on the silicon oxide.

Following the above description, the dielectric layer 20 according to the present invention includes a heating device 30 and two electrodes 40 buried in the dielectric layer 20. Alternatively, they can be disposed on the dielectric layer 20. The heating device 30 is connected with a power supply and used for receiving the electrical energy of the power supply and converting it to thermal energy, which is provided to the gas sensor according to the present invention for detecting gas. In order to make the provided thermal energy stable, the material of the heating device 30 according to the present invention is primarily noble metals. Based on the above property, the material of the heating device 30 is selected from the group consisting of titanium, platinum, gold, silver, and tantalum. In addition, the twp electrodes 40 and the heating device 30 are electrically insolated. Besides, the two electrodes 40 are connected with the sensing layer 50 for measuring the current and voltage changes produced by the reactions in the sensing layer 50 and thus judging the gas concentration in the environment.

According to the miniature gas sensor as described above, the sensing layer 50 provided by the present invention is used for contacting and reacting with the target gas in the monitoring environment. As the target gas contacts and reacts with the material of the sensing layer 50, free electrons will be produced. The free electrons will change the voltage level of the sensing layer 50 and generate current. The two electrodes 40 connected with the sensing layer 50 will measure them and thus achieving the purpose of the sensing the gas. The sensing layer 50 includes a metal oxide layer 510 and a reaction layer 520. The reaction processes of the material of the reaction layer 520 and the target gas have been described above. Hence, the details will not described again. In addition, the metal oxide layer 510 provided by the present invention is used as a conductor for conducting electrons. To enable the function of conducting electrons more rapid and sensitive, the metal oxide layer 510 according to the present invention adopts a single material. Based on the above description, the metal oxide layer 510 according to the present invention is selected from the group consisting of tungsten trioxide, zinc oxide, and tin dioxide.

According to the miniature gas sensor as described above, the sensing layer 50 further including a supporting layer (not shown in figures). The supporting layer is composed of a silicon dioxide layer and a silicon nitride layer. The thickness of the silicon dioxide layer is between 500 nm and 1500 nm and the thickness of the silicon nitride layer is between 50 nm and 250 nm.

Figure 2:
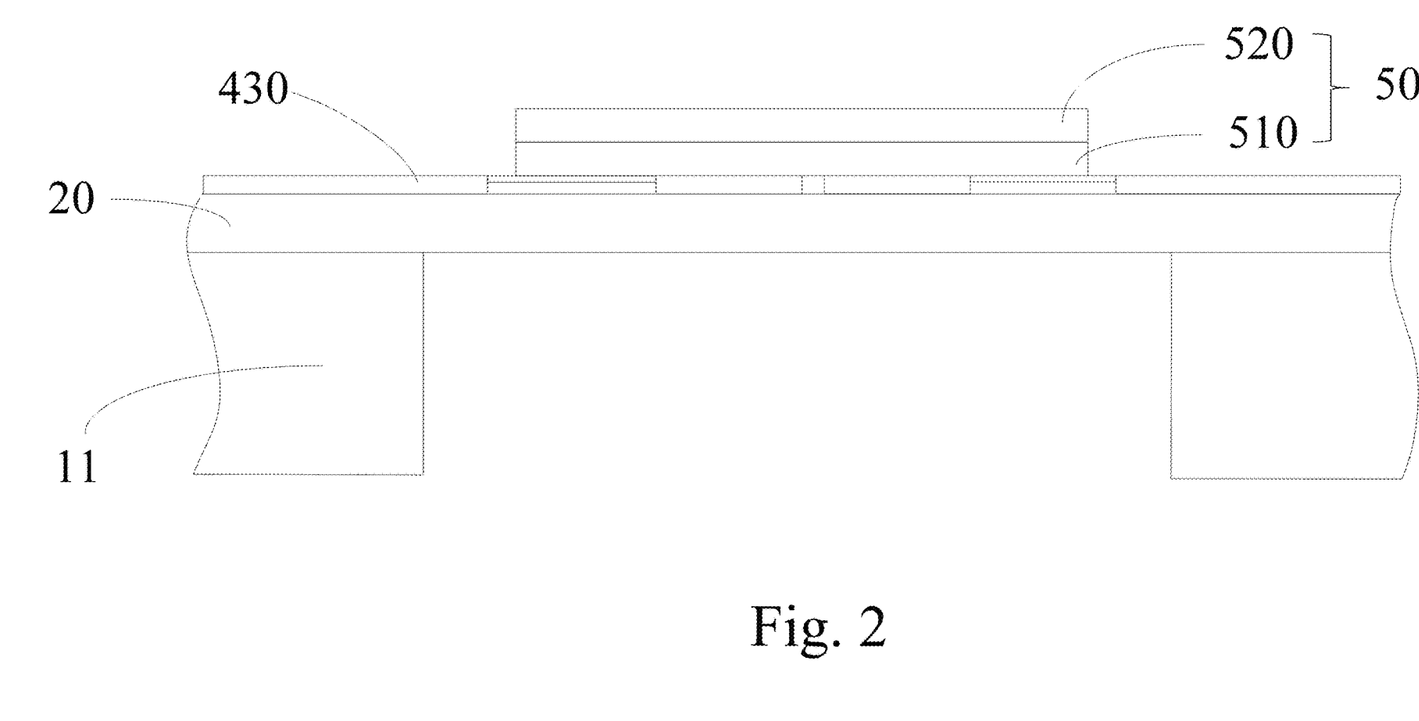
FIG. 2 shows a cross-sectional view according to a second embodiment of the present invention.

Please refer to FIG. 2, which shoes another embodiment of the present invention. As shown in the figure, the substrate 11 of the gas sensor is a discontinuous structure such that the dielectric layer 20 is built on stilts above the substrate 11 and producing a heat dissipating region 201 not contacting the substrate 11 directly. By including the heat dissipating region 201, the heat generated by the heating device 30 can be regulated effectively and preventing overheating of the overall temperature of the gas sensor. Consequently, the thermoelectric effect can be reduced, and hence the stability and accuracy of the gas sensor can be enhanced.

Figure 3:
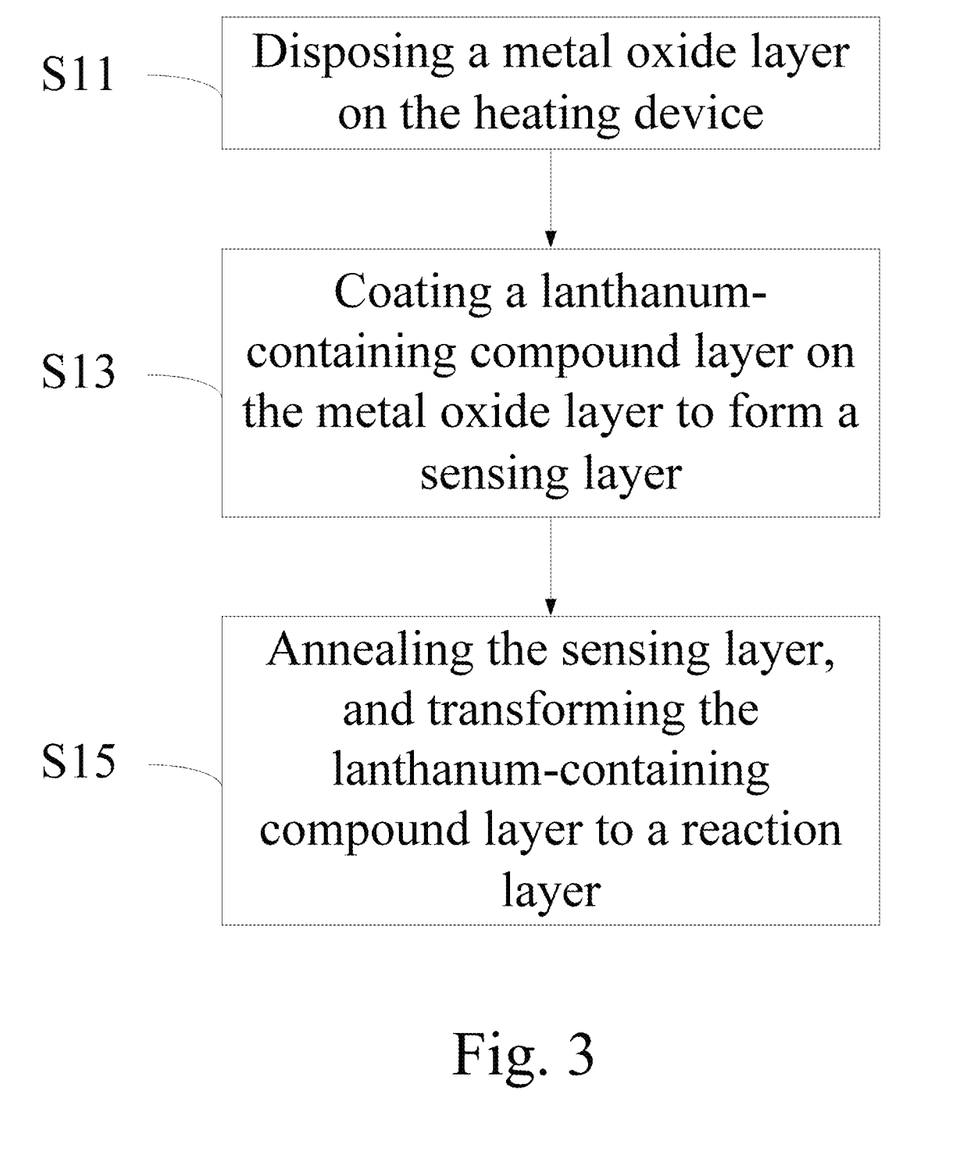
FIG. 3 shows a manufacturing flowchart according to a preferred embodiment of the present invention.

Next, by referring to FIG. 3, which shows a manufacturing flowchart of the present invention, the method for manufacturing the miniature gas sensor will be described. The miniature gas sensor according to the present invention is a semiconductor gas sensor, which comprises a substrate, a dielectric layer, a heating device, two electrodes, and a sensing layer. The method for manufacturing the miniature gas sensor comprises steps of:

Step S11: Disposing a metal oxide layer on the heating device;

Step S13: Coating a lanthanum-containing compound layer on the metal oxide layer to form a sensing layer; and Step S15: Annealing the sensing layer, and transforming the lanthanum-containing compound layer to a reaction layer.

As in the step S11, according to the method for manufacturing the miniature gas sensor provided by the present invention, a metal oxide layer is provided as the conductor for conducting electrons. The metal oxide layer is disposed by deposition, which includes chemical vapor deposition or physical vapor deposition. In addition, in order to provide sufficient conducting capability for electrons and avoid influences of the heating process on material properties, the material of the metal oxide is selected from, but not limited to, the group consisting of tungsten trioxide, zinc oxide, and tin dioxide.

As in the step S13, according to the method for manufacturing the miniature gas sensor provided by the present invention, a lanthanum-containing compound layer is coated on the metal oxide layer to form a sensing layer. The coating method can include spin coating, chemical vapor deposition, or physical vapor deposition. In addition, the lanthanum-containing compound is a compound capable of providing heat and converting to lanthanum oxide. Accordingly, the material of the lanthanum-containing compound layer is selected from the group consisting of lanthanum hydroxide and lanthanum carbonate. In order to enable the coated sensing layer to have excellent sensing capability and electron conduction, the thickness of the lanthanum-containing compound layer should be controlled to between 0.1 μm and m for facilitating the lanthanum-containing compound layer to contact carbon dioxide molecules as we as conducting electrons rapidly. Based on the above description, according to a preferred embodiment of the present invention, the layer is prepared by first mixing lanthanum hydroxide, isopropanol, and solubilizer and then coating a lanthanum-containing compound layer between 0.1 μm and 5 μm.

As in the step S15, according to the method for manufacturing the miniature gas sensor provided by the present invention, the sensing layer is annealed for transforming the lanthanum-containing compound layer to a reaction layer. Because the lanthanum-containing compound layer is not able to react with the carbon dioxide molecules in the environment under detection and generate electron current, an annealing step is required for transforming the lanthanum-containing compound to lanthanum oxide by heating. According to a preferred embodiment of the present invention, the annealing temperature in the annealing step is between 300° C. and 600° C.

Figure 4A:
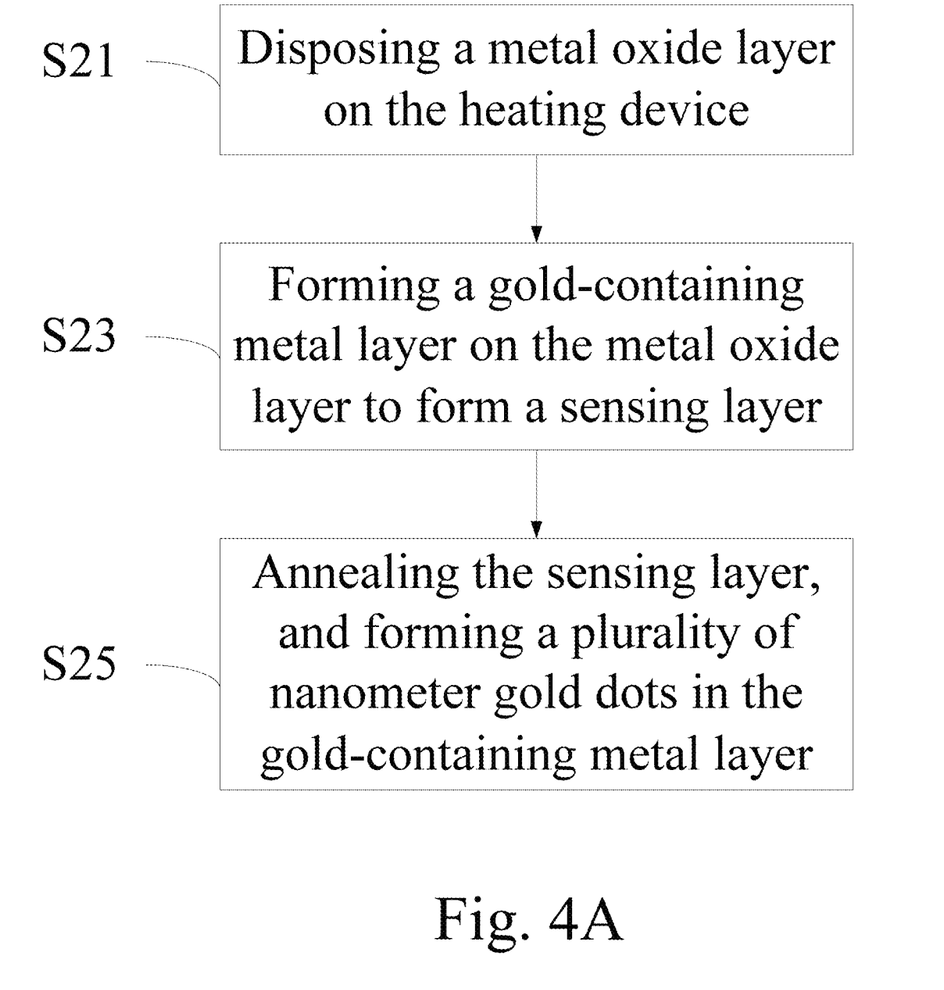
FIGS. 4A and 4B show manufacturing flowcharts according to another preferred embodiment of the present invention.

Next, by referring to FIG. 4A, which shows a manufacturing flowchart of the present invention, the method for manufacturing the miniature gas sensor will be described. The miniature gas sensor according to the present invention is a semiconductor gas sensor, which comprises a substrate, a dielectric layer, a heating device, two electrodes, and a sensing layer. The method for manufacturing the miniature gas sensor comprises steps of:

Step S21: Disposing a metal oxide layer on the heating device;

Step S23: Forming a gold-containing metal layer on the metal oxide layer to form a sensing layer; and Step S25: Annealing the sensing layer, and forming a plurality of nanometer gold dots in the gold-containing metal layer.

As in the step S21, according to the method for manufacturing the miniature gas sensor provided by the present invention, a metal oxide layer is provided on the heating device. The preparation method and the material are identical to those in the step S11. Hence, the details will not be described again.

As in the step S23, according to the method for manufacturing the miniature gas sensor provided by the present invention, a gold-containing metal layer is coated on the metal oxide layer to form a sensing layer. The gold-containing metal layer can be coated by deposition, which includes chemical vapor deposition or physical vapor deposition. Because this gold-containing metal layer is only a temporary coating structure, the coating thickness is between 1nm and 30 nm, preferably 3 nm to 15 nm, to avoid failure in forming nanometer gold dots by annealing due to the excessive thickness. Thereby, a plurality of nanometer gold dots can be formed using gold.

Figure 5:
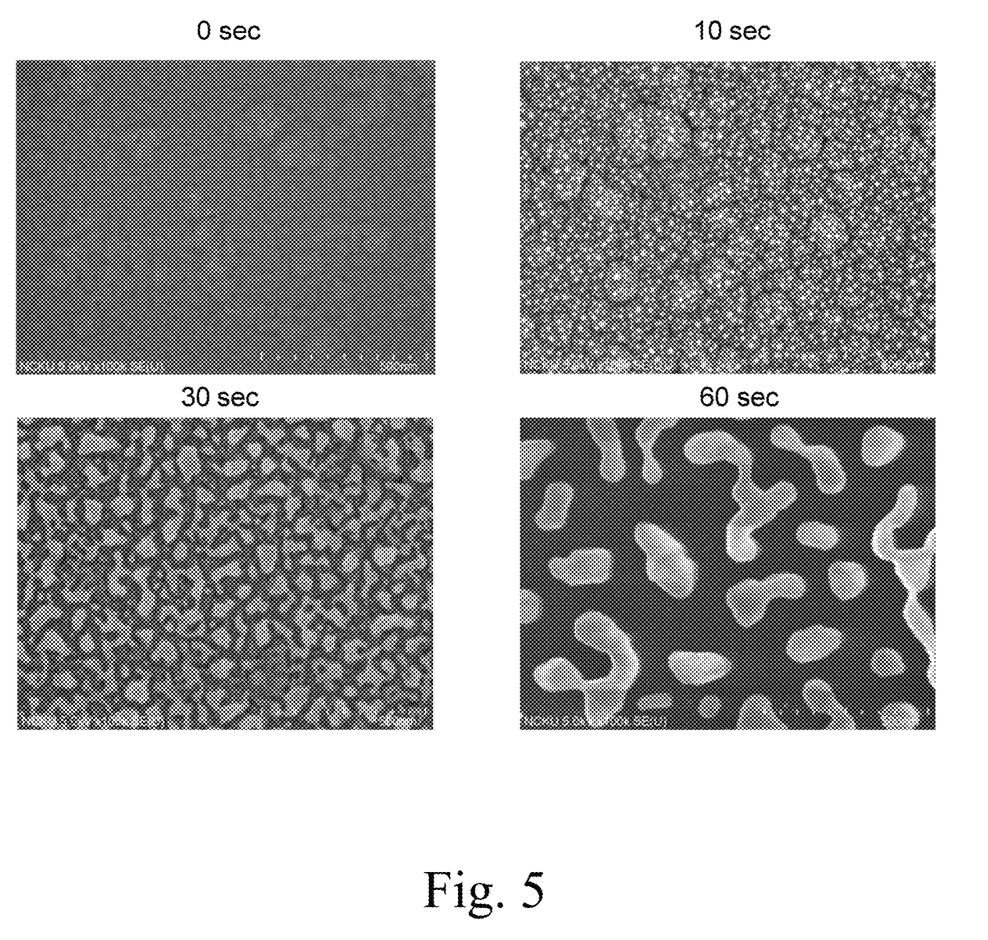
FIG. 5 shows the relation between the structure of the sensing layer and the annealing time according to a preferred embodiment of the present invention.

As in the step S25, according to the method for manufacturing the miniature gas sensor provided by the present invention, annealing is performed on the sensing layer to form a plurality of nanometer gold dots in the gold-containing metal layer and thus providing sufficient electrical conductivity for conducting the produced electrons by the reaction on the surface of the sensing layer. As shown in FIG. 5, the process of forming nanometer gold dots in the gold-containing metal layer is closely related to the reaction time. The gap between two nanometer gold dots is extended as the annealing time is increased. Thereby, in order to make the nanometer gold dots have the superior electron conduction efficiency, according to a preferred embodiment of the present invention, the annealing time in the annealing step should be between 10 and 60 seconds and preferably between 20 and 40 seconds. In addition, the annealing temperature in the annealing step is between 300° C. and 600° C.

Figure 4B:
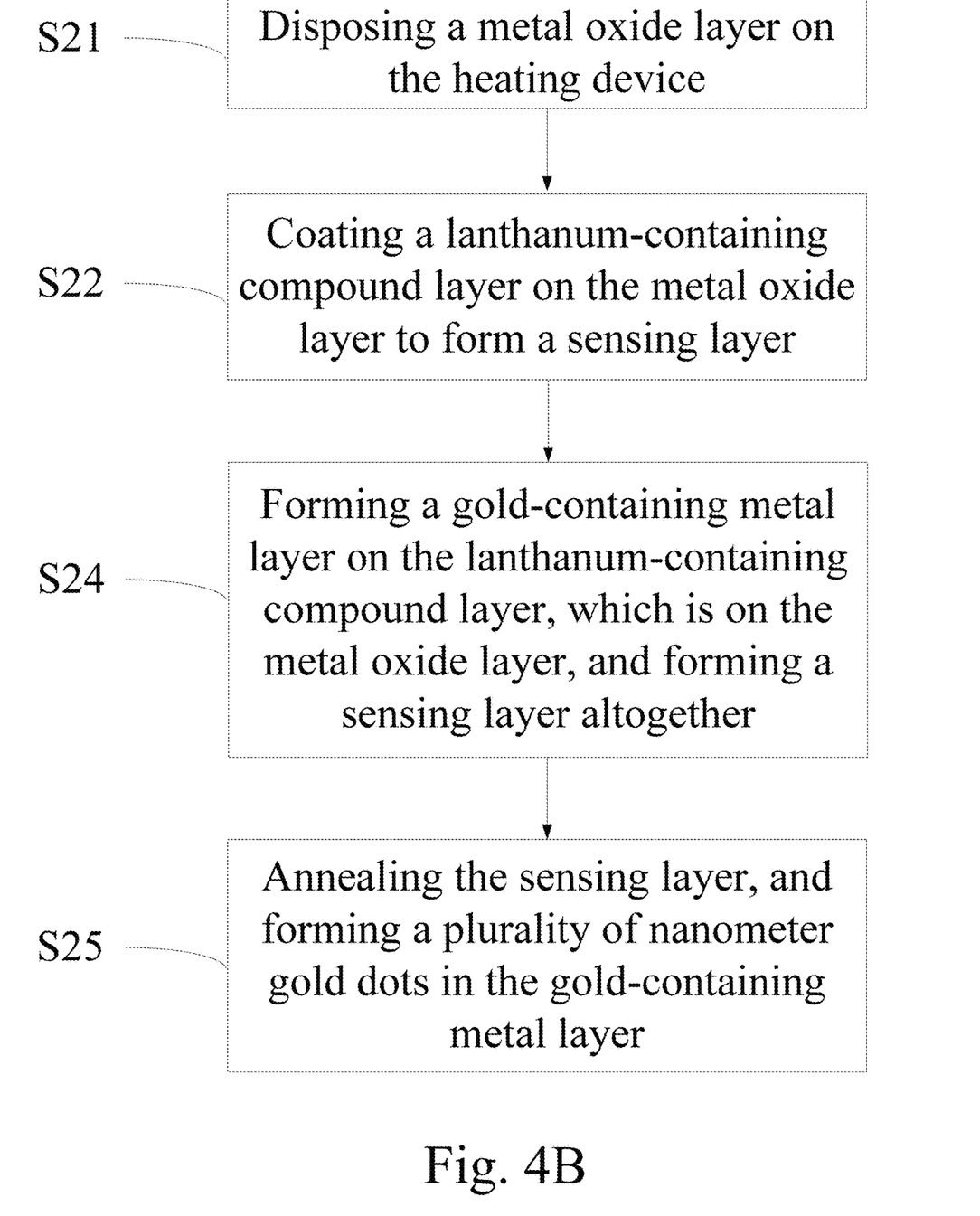

Furthermore, referring to the manufacturing flowchart shown in FIG. 4B, according to the method for manufacturing the miniature gas sensor provided by the present invention, before forming a gold-containing metal layer on the metal oxide layer, a lanthanum-containing compound layer can be coated on the metal oxide layer. As shown by the steps S22 and S24 in FIG. 4B, according to another preferred embodiment of the present invention, after disposing a metal oxide layer on the heating device, a lanthanum-containing compound layer is first coated on the metal oxide layer. Then a gold-containing metal layer is coated on the lanthanum-containing compound layer, which is on the metal oxide layer, and hence forming a sensing layer altogether. Finally, the sensing layer is annealed to form a plurality of nanometer gold dots in the gold-containing metal layer. In the step of coating the lanthanum-containing compound layer, the coating method includes spin coating, pray coating, screen printing, dispensing or physical vapor deposition (RF sputter). Besides, in the step of coating the lanthanum-containing compound layer, the adopted material of the lanthanum-containing compound layer is selected from the group consisting of lanthanum hydroxide and lanthanum carbonate.

The miniature gas sensor prepared according to any of the above method for manufacturing can be used for detecting carbon monoxide. When carbon monoxide is present and as the temperature increases, carbon monoxide will be decomposed into carbon dioxide and free electrons. The free electrons will increase the surface conductivity of the sensing layer and hence lowering the resistivity. Thereby, the resistance is decreased as the concentration is increased. Thereby, the concentration of carbon monoxide in the environment can be detected effectively.

In the following, the technical contents, characteristics, and results of practical embodiments according to the present invention are described. Nonetheless, the present invention is not limited to embodiments.

Embodiment 1

Figure 6A:
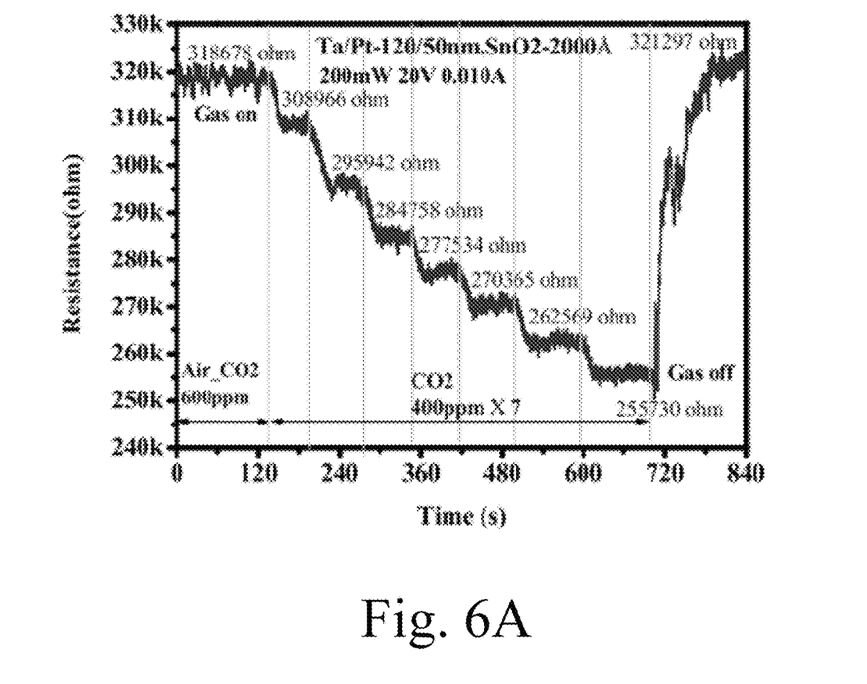
FIGS. 6A to 6C show diagrams of gas sensing performance according to a preferred embodiment of the present invention.

Tests on Structural Properties of a Lanthanum-Containing-Compound Miniature Gas Sensor Please refer to FIG. 6A, which shows the relation between the sensing time and resistance while sensing carbon dioxide using the lanthanum-containing-compound miniature gas sensor according to the present invention. As shown in the figure, for the first 120 seconds, the concentration of carbon dioxide in the environment under test is 600 ppm. In the following 10 minutes, the concentration of carbon dioxide in the environment under test is increased by 400 ppm for seven times and the variation in resistance of the lanthanum-containing-compound miniature gas sensor is observed. According to the figure, it is observed that the resistance of the gas sensor will be lowered to a stable value rapidly for every increase in the concentration of carbon dioxide in the environment under test. The stable value will be maintained until the next increase in the concentration of carbon dioxide in the environment under test. The difference between the initial resistance value and the final one can reach 60 thousand ohms. Accordingly, the stability and the wide sensing of the gas sensor are apparent. Finally, when the supply of carbon dioxide is stopped and the concentration of carbon dioxide in the environment under test returns to the initial condition, the resistance value of the gas sensor can recover to the initial value in a short time with little difference with the resistance value before the test. Hence, the gas sensor is highly stable.

Figure 6B:
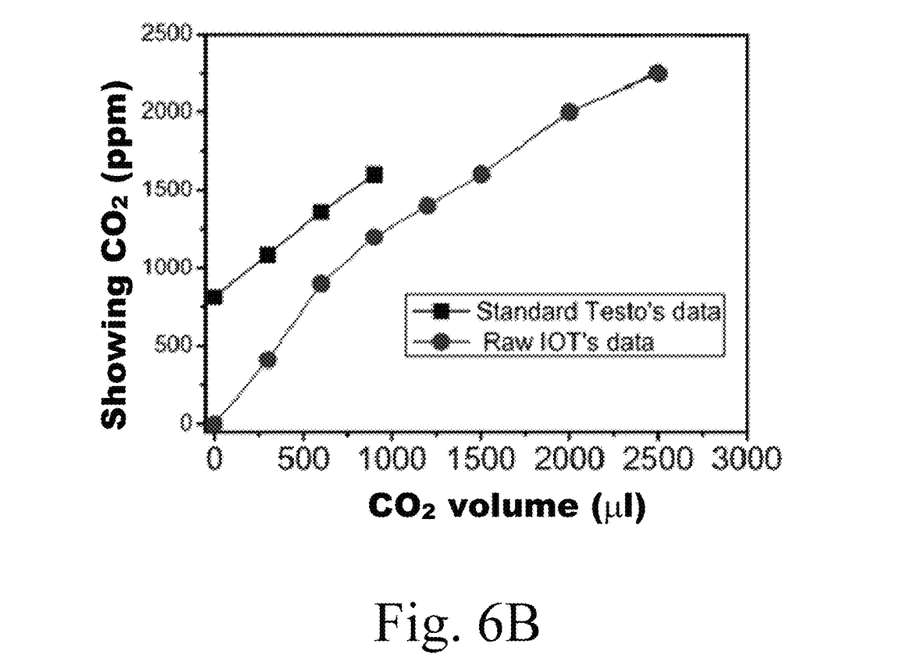

Please refer to FIG. 6B, which shows comparisons of the measurement results between the lanthanum-containing-compound miniature gas sensor according to the present invention and the commercial carbon-dioxide gas sensor. The square data are the results by the commercial carbon-dioxide gas sensor; circle data are the results by the lanthanum-containing-compound miniature gas sensor according to the present invention. As shown in the figure, the gas sensor provided by the present invention can sense in a larger concentration range of carbon dioxide. In addition, the results are more accurate. It is obviously that the lanthanum-containing-compound miniature gas sensor according to the

Embodiment 2

Tests on Structural Properties of a Nanometer-Gold Miniature Gas Sensor

Figure 6C:
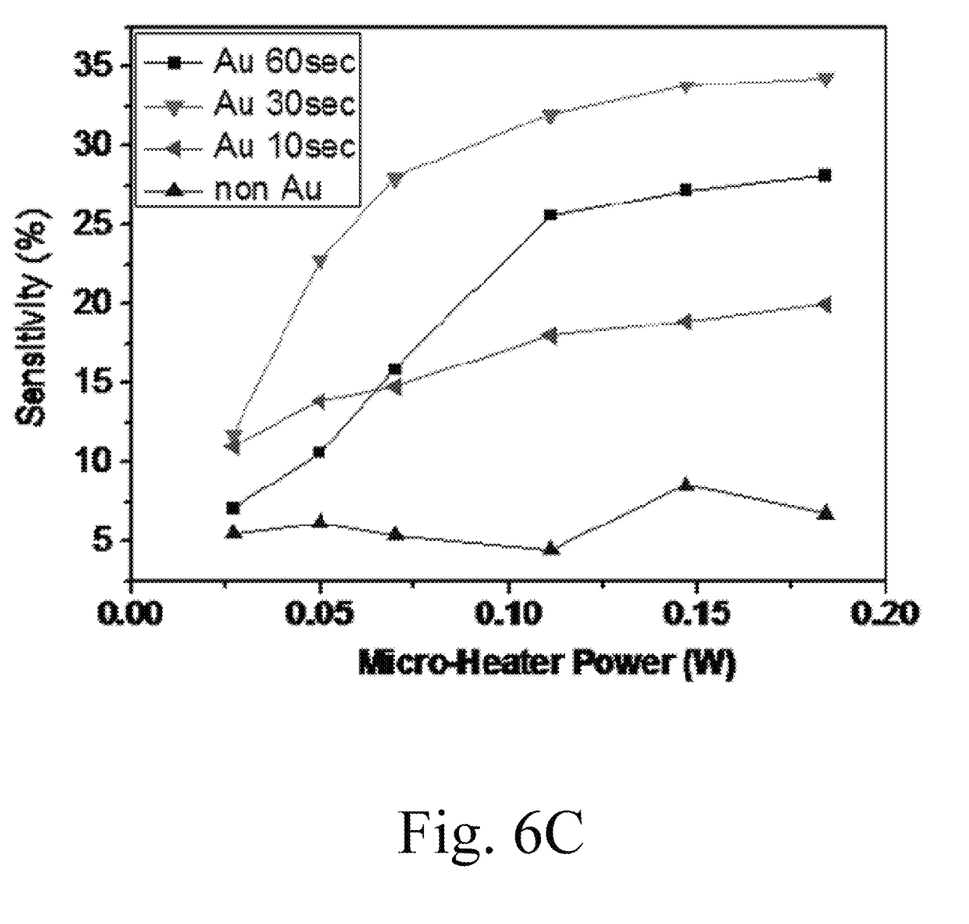

Please refer to FIG. 6C, which shows the trend of sensitivity versus the power of the miniature gas sensor in a carbon monoxide environment with varying annealing times for the nanometer-gold miniature gas sensor according to the present invention. As shown in the figure, when the gold-containing metal layer is not annealed (namely, 0 second), owing to inexistence of nanometer gold dots in the gold-containing metal layer, the capability in sensing gas will not increase as the miniature gas sensor operates (by increasing the heating power of the sensor). In addition, for other gas sensors prepared by different annealing times, although they demonstrate similar trend of changes in resistance, the miniature gas sensor annealed for 30 seconds owns the greatest sensitivity (~35%); its variation is more stable than those annealed for 10 and 60 seconds. It is apparent that the distribution of nanometer gold dots for 30-second annealing is the most complete and appropriate and capable of absorbing more carbon monoxide. Thereby, the sensitivity is the highest and the measured values will be the most accurate.

To sum up, the present invention provides a highly stable miniature gas sensor and the method for manufacturing the same. By disposed a sensing layer with a different material on a semiconductor structure, gas sensing can be performed effectively. The problems of current gas sensors, particularly carbon dioxide sensors, including bulky size, high price, and difficulty in miniaturization, can be solved. By providing a novel miniature gas sensor structure, the volume of gas sensors can be reduced effectively and hence increasing their applications. In addition, by using lanthanum carbonate or nanometer gold as the sensing material of the semiconductor gas sensor, the sensitivity and the accuracy of the gas sensor can be improved effectively.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. A miniature gas sensor, comprising a substrate, a dielectric layer, and a sensing layer, said dielectric layer disposed on said substrate, and a heating layer and at least a pair of sensing electrodes buried in said same dielectric layer while said two electrodes and said heating device are electrically insulated, said sensing electrodes having interdigitized sensing elements, said heating layer including a heating element, two second connecting elements and two heating pads, said heating element surrounding said interdigitized sensing elements, said two second connecting elements connected with said heating element and said two heating pads, wherein said sensing layer is disposed on said heating layer and said at least one sensing electrode, said sensing layer is connected with said sensing electrodes, and further said sensing layer is composed of a metal oxide layer and a reaction layer, wherein said reaction layer is disposed on said metal oxide layer, said reaction layer contacts and reacts with gas, said metal oxide layer is composed of a single material for conducting electrons.

2. The miniature gas sensor of claim 1, wherein said substrate is a discontinuous structure such that said dielectric layer is built on stilts above said substrate and producing a heat dissipating region not contacting said substrate directly.

3. The miniature gas sensor of claim 1, wherein the material of said reaction layer is selected from the group consisting of lanthanum carbonate and nanometer gold.

4. The miniature gas sensor of claim 3, wherein a thickness of lanthanum carbonate is between 0.1 and 4 µm and a thickness of nanometer gold is 1-30 nm.

5. The miniature gas sensor of claim 1, wherein the material of said metal oxide layer is selected from the group consisting of tungsten trioxide, zinc oxide, and tin dioxide.

6. The miniature gas sensor of claim 1, wherein the material of said heating device is selected from the group consisting of titanium, gold, platinum, silver, and tantalum.

7. The miniature gas sensor of claim 1, wherein the material of said dielectric layer is selected from the group consisting of silicon nitride, silicon oxide, and silicon oxynitride.

8. A miniature gas sensor, comprising a substrate, a dielectric layer, and a sensing layer, said dielectric layer disposed on said substrate, and a heating layer and at least a pair of sensing electrodes, said sensing electrodes having interdigitized sensing elements, said heating layer including a heating element, two second connecting elements and two heating pads, said heating element surrounding said interdigitized sensing elements, said two second connecting elements connected with said heating element and said two heating pads, said heating layer and said sensing electrodes buried in said same dielectric layer while said two electrodes and said heating device are electrically insulated, wherein said sensing layer is disposed on said heating layer and said sensing electrode, said sensing layer is connected with said sensing electrode, and further said sensing layer is composed of a metal oxide layer and a reaction layer, wherein said reaction layer is disposed on said metal oxide layer, said reaction layer contacts and reacts with gas, said metal oxide layer is composed of a single material for conducting electrons.

9. The miniature gas sensor of claim 8, wherein said sensing layer is disposed on a supporting layer.

10. The miniature gas sensor of claim 9, wherein said supporting layer is composed of a silicon dioxide layer and a silicon nitride layer.

11. The miniature gas sensor of claim 10, wherein the thickness of said silicon dioxide layer is between 500 nm and 1500 nm and the thickness of said silicon nitride layer is between 50 nm and 250 nm.

12. The miniature gas sensor of claim 8, wherein said sensing electrodes further including a sensing part, two first connecting parts and two electrode pads; said sensing part including two interdigitated sensing elements that are staggered and two extension parts parallel disposed on said interdigitated sensing elements; said extension parts are connected to said first connecting parts respectively; said first connecting parts are connected to said electrode pads respectively.

13. The miniature gas sensor of claim 8, wherein said heating layer further including said heating element, said two second connecting elements and two heating pads; a plurality of U-shape part arranged in a head-to-tail arrangement to form said heating element and said heating element including a first end and a second end; said heating element surrounding said interdigitated sensing elements and forming a notch; said first end and said second end are connected to said second connecting element respectively; said second connecting elements are connected to said heating pads respectively.

14. A miniature gas sensor, comprising a substrate, a dielectric layer, and a sensing layer, said dielectric layer disposed on said substrate, and a heating device and two electrodes, said electrodes having interdigitized sensing elements, said heating device including a heating element, two second connecting elements and two heating pads, said heating element surrounding said interdigitized sensing elements, said heating element and said interdigitized sensing elements buried in said same dielectric layer while said said heating element and said interdigitized sensing elements are electrically insulated, wherein said sensing layer is disposed on said heating device and said sensing two electrodes, said sensing layer is connected with said two electrodes, and further said sensing layer is composed of a metal oxide layer and a reaction layer, wherein said reaction layer is disposed on said metal oxide layer; wherein said substrate is a discontinuous structure such that said dielectric layer is built on stilts above said substrate and producing a heat dissipating region not contacting said substrate directly, said reaction layer contacts and reacts with gas, said metal oxide layer is composed of a single material for conducting electrons.

15. The miniature gas sensor of claim 14, wherein said heating device and said two electrodes can be further disposed on said dielectric layer.

16. The miniature gas sensor of claim 14, wherein the material of said reaction layer is selected from the group consisting of lanthanum carbonate and nanometer gold.

17. The miniature gas sensor of claim 14, wherein the material of said metal oxide layer is selected from the group consisting of tungsten trioxide, zinc oxide, and tin dioxide.

18. The miniature gas sensor of claim 14, wherein the material of said heating device is selected from the group consisting of titanium, gold, platinum, silver, and tantalum.

19. The miniature gas sensor of claim 14, wherein the material of said dielectric layer is selected from the group consisting of silicon nitride, silicon oxide, and silicon oxynitride.

20. A miniature gas sensor, comprising a substrate, a dielectric layer, and a sensing layer, said dielectric layer is disposed on said substrate, a heating layer and at least one sensing electrode buried in said same dielectric layer while said heating layer and said sensing electrode are electrically insulated, wherein said sensing layer is disposed on said dielectric layer, and said sensing layer is connected with said sensing electrode, and further said sensing layer is composed of a metal oxide layer and a reaction layer, wherein said reaction layer is disposed on said metal oxide layer, said reaction layer contacts and reacts with gas for producing free electrons, said metal oxide layer conducting said free electrons to make said sensing layer generate current to said sensing electrode.

* * * * *